United States Patent [19]

Becher et al.

[11] Patent Number: 4,918,227
[45] Date of Patent: Apr. 17, 1990

[54] PROCESS FOR THE PREPARATION OF BENZOYL UREAS

[75] Inventors: Heinz M. Becher, Bingen am Rhein; Rudolf Mengel, Gau-Algesheim; Walter Ost, Bingen am Rhein, all of Fed. Rep. of Germany

[73] Assignee: Shell Internationale Research Naatschappy B.V., Netherlands

[21] Appl. No.: 6,552

[22] PCT Filed: Mar. 6, 1986

[86] PCT No.: PCT/EP86/00116
§ 371 Date: Feb. 9, 1987
§ 102(e) Date: Feb. 9, 1987

[87] PCT Pub. No.: WO86/05487
PCT Pub. Date: Sep. 25, 1986

[30] Foreign Application Priority Data
Mar. 14, 1985 [DE] Fed. Rep. of Germany ....... 3509075

[51] Int. Cl.$^4$ ........................................... C07C 127/22
[52] U.S. Cl. ........................................................ 564/44
[58] Field of Search .......................................... 564/44

[56] References Cited
U.S. PATENT DOCUMENTS
4,005,223 1/1977 Sirrenberg et al. .................... 564/44
4,085,226 4/1978 Sirrenberg et al. .................... 564/44

OTHER PUBLICATIONS

*Methoden der Organischen Chemie*, vol. E4, Kohlensaure-Denivate, 1983, George Thieme Verlag, pp. 763–764.

Primary Examiner—Mary C. Lee
Assistant Examiner—Zinna Northington-Davis
Attorney, Agent, or Firm—Sughrue, Mion, Zinn, Macpeak & Seas

[57] ABSTRACT

Benzoyl ureas of the formula

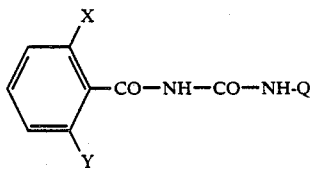

are prepared by starting from benzoyl derivatives of the formula Q—COHal which are converted via the corresponding azides into the isocyanates, which are in turn reacted with corresponding benzamides.

2 Claims, No Drawings

PROCESS FOR THE PREPARATION OF BENZOYL UREAS

This invention relates to a novel process for the preparation of benzoyl ureas, which are useful as pesticides.

THE PRIOR ART

It is known to prepare benzoyl ureas by reacting a corresponding benzoic acid amide with a substituted phenylisocyanate. The isocyanate starting compound may be prepared from a corresponding aniline by reaction with phosgene. The aniline itself may be obtained from the corresponding nitro compound by reduction.

DESCRIPTION OF THE INVENTION

We have discovered that there is a new reaction sequence which provides a technically simple method of preparing benzoyl ureas of the formula

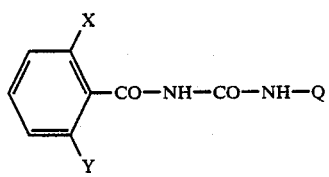
(I)

wherein
X is hydrogen, fluorine or chlorine;
Y is fluorine, chlorine, $CH_3$ or $CF_3$; and
Q is

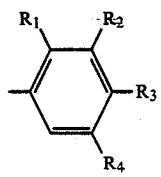

where
$R_1$, $R_2$ and $R_4$ are each independently fluorine, chlorine, bromine, $CF_3$, $OCF_3$ or hydrogen;
$R_3$ is fluorine, chlorine, bromine, $CF_3$, $OCF_3$, hydrogen, ethoxy substituted by four to five fluorine and/or chlorine atoms, phenyl which is mono- or polysubstituted by fluorine, chlorine, bromine, $CH_3$, $CF_3$, $OCF_3$, $OCF_2CHF_2$ $OC_2F_5$, $NO_2$ or CN; or pyridyloxy which is mono- or polysubstituted by fluorine, chlorine or $CF_3$; or $R_2$ and $R_3$ or $R_3$ and $R_4$, together with each other, are —O—$CF_2$—$CF_2$—O—.

X and Y are preferably the pairs F/H, F/F, Cl/H, Cl/Cl or Cl/F. Examples of Q are:
-4-Chlorophenyl,
-2,3,4,5-tetrafluorophenyl,
-2,3,4,5-tetrachlorophenyl,
-3,5-dichloro-2,4-difluorophenyl,
-3,5-dichloro-4-pentafluoroethoxyphenyl,
-3,5-Dichloro-4-[1,1,2,2-tetrafluoroethoxy]phenyl,
-3,5-Dichloro-4-trifluoromethoxyphenyl,
-3,5-Dichloro-4-[(3-chloro-5-trifluoromethyl-pyridin-2-yl)oxy]phenyl,
-3-Chloro-4-[(3-chloro-4-trifluoromethyl)phenoxy]phenyl,
-3-(4-Trifluoromethylphenoxy)-phenyl,
-3-(3-Trifluoromethylphenoxy)-phenyl,
-3-(2-Trifluoromethylphenoxy)-phenyl,
-3,4-(Tetrafluoroethylenedioxy)-phenyl,
-4-Trifluoromethylphenyl and
-4-Trifluoromethoxyphenyl.

The various substituents may be identical or different within the scope of the above definition. Alkyl groups may be straight-chained or branched. In the case of polysubstitution, CN, $CF_3$, $OCF_3$, $OC_2F_5$, $OCF_2$—$CF_2H$ occur only once, whereas halogen atoms, either identical or different, may occur up to six times.

The process according to the invention proceeds through the following stages:

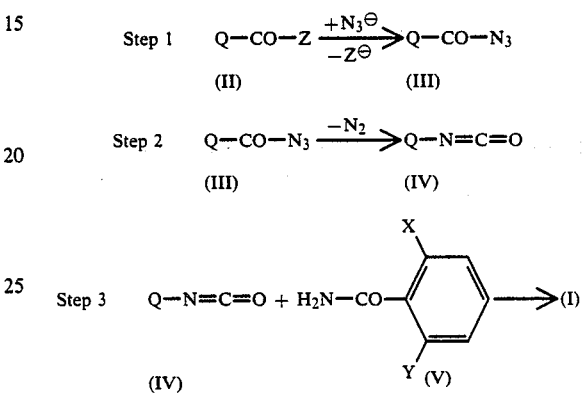

In formula (II) Z is a substituent which may be replaced by the azide ion.

Examples includes: fluorine, chlorine, bromine, iodine and groups of the formula O—$R_6$ wherein $R_6$ is lower alkyl, phenyl, benzyl, lower alkoxycarbonyl, phenoxycarbonyl, lower alkylcarbonyl or benzoyl.

The halogens fluorine and chlorine are preferred.

Lower alkyl radicals are methyl, ethyl, propyl, isopropyl, n-butyl, isobutyl, sec.butyl and tert.butyl.

Examples of azides include sodium azide, potassium azide and calcium azide.

The steps may be carried out one after the other in the same reaction medium without isolation of the intermediate products. Steps 1 and 2 are carried out at temperatures between about 80° C. and the boiling point of the reaction mixture, taking care to avoid temperatures above 180° C. The range between about 100° and 140° C. is preferred. The reaction constitutes thermal degradation of a carboxylic acid via the carboxylic acid azide to yield the isocyanate by Curtius degradation. Decomposition of the azide is effected so that no substantial quantities thereof remain in the reaction mixture. Suitable solvents include, in particular, halogenated benzenes, such as chlorobenzene, dichlorobenzene and high-boiling-point ethers, and also aromatic hydrocarbons such as toluene.

Further reaction of the isocyanate with the amide V is carried out by adding the amide V to the solution of the isocyanate and stirring the mixture at temperatures between about 80° and 160° C., preferably between 90° and 130° C. Depending on the reactivity of the components and the reaction temperature, the reaction time is up to several hours.

The method of synthesis according to the present invention via the compounds III, which have heretofore not been described, makes it possible to avoid the highly undesirable reaction with phosgene (VIII).

The compounds of the formula I are obtained with good yields and high purity without isolation of the intermediate in the individual steps.

Examples of the compounds which may advantageously be prepared according to the invention are the compounds disclosed in German Offenlegungsschriften 23 23 236, 25 04 982, 25 97 944, 25 31 279, 25 37 413, 26 01 780, 27 26 684, 30 03 112, 30 26 825, 30 41 947, 32 23 505, 32 32 265 and 32 35 419 and in published European applications 52 833 and 57 888.

The following compounds should be mentioned in particular:

N-(2,4-Difluoro-3,5-dichlorophenyl)-N'-(2,6-difluorobenzoyl)-urea,

N-(3,5-Dichloro-4-pentafluoroethoxyphenyl)-N'-(2,6-difluorobenzoyl)-urea,

N-[3,5-Dichloro-4-(1,1,2,2-tetrafluoroethoxy)phenyl]-N'-(2,6-difluorobenzoyl)-urea, N-(2,3,4,5-Tetrafluorophenyl)-N'-(2,6-difluoro-benzoyl)-urea, N-(2,3,4-Trifluoro-5-chlorophenyl)-N'-(2,6-difluorobenzoyl)-urea, N-(2,3,4,5-Tetrachlorophenyl)-N'-(2,6-difluoro-benzoyl)-urea, N-[3,5-Dichloro-4-(3-chloro-5-trifluoromethylpyridin-2-yloxy)-phenyl]-N'-(2,6-difluorobenzoyl)-urea, N-(4-Methoxyphenyl)-N'-(2-chlorobenzoyl)-urea, and N-(4-Trifluoromethylphenyl)-N'-(2,6-difluoro-benzoyl)-urea.

With regard to the correlation between structure and activity in benzoyl ureas with an insecticidal effect, it is known that compounds which are mono- or disubstituted in the ortho-position in the benzoyl moiety of formula I and compounds which are mono- or disubstituted in the meta-position in the aniline moiety of formula I are particularly effective. In the aniline moiety the ortho- and/or para-position may be free or substituted.

Conventional methods of synthesizing benzoyl ureas of the formula I comprise the folling reaction sequences:

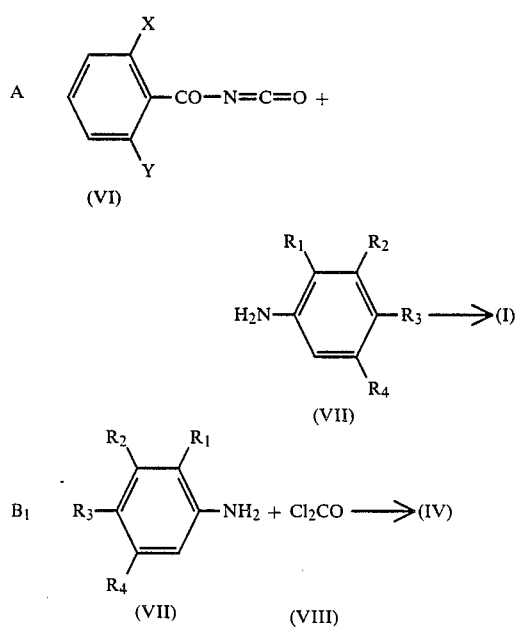

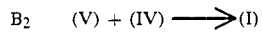

In method A as well as in method B of the conventional syntheses, the aniline moiety is introduced into the synthesis either directly in the form of an aniline (VII) or in a preceding phosgenation step $B_1$ in the form of the isocyanate (IV).

On the one hand, the amino group of the aniline (VII) as a substituent in electrophilic aromatic substitution reactions directs the newly introduced electrophile preferably into the ortho or para position. On the other hand, however, compounds of the formula (I) show particularly good insecticidal activity when they carry one or more, preferably halogen substituents in the meta-position of the aniline moiety. This means, that, in order to prepare the aniline (VII), it is not possible to start from the aniline (VII, $R_1$–$R_4$=H) or from suitable anilines substituted by $R_1$ and $R_4$ (VII, $R_3$, $R_5$-H), but rather that an alternative route must be found via a nitrobenzene (IX)

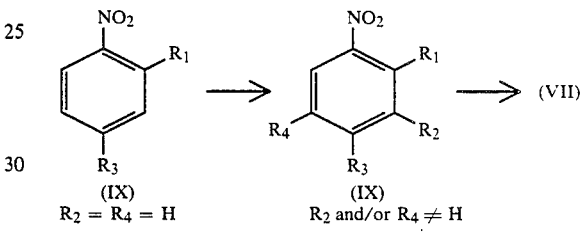

in which the substituents $R_2$ and/or $R_4$ are introduced by making use of the meta-directing effect of the nitro group. The nitro compound (IX) is then reduced to form the aniline (VII).

By contrast, the process according to the present invention starts from a benzoic acid derivative of the formula (II) in which the carboxylic acid function in (II) as a meta-directing substituent may also advantageously be used to build up the substitution pattern $R_1$ to $R_4$ by means of nucleophilic and electrophilic substitution reactions in the benzene ring:

in order to introduce halogen substituents: possibly starting from benzoyl chloride by stepwise chlorination to form the mono-, di-, tri- or tetra-chlorobenzoylchloride.

In order to create the 2,4-dichloro-3,5-dichlorophenyl substitution known from German Offenlegungsschrift 30 44 055 from 2,3,4,5-tetrachlorobenzoyl chloride with fluoride ions to form the 2,4-difluoro-3,5-dichlorobenzoylfluoride, possibly analogously to published European application 164 619.

In halogen exchange reactions, such as chlorine-fluorine exchange, if benzoylchlorides are used as starting materials, apart from the halogen exchange in the nucleus of the aromatic ring the halogen of the acid halide function is also exchanged, and the resulting benzoyl fluoride (II) (Z=F) reacts with azides in reaction step 1 more rapidly and totally than the corresponding acid chloride (II) (Z=Cl).

The following examples illustrate the present invention and will enable others skilled in the art to understand it more completely. It should be understood, however, that the invention is not limited solely to the particular examples given below.

EXAMPLE 1

N-(2,3,4-Trifluoro-5-chlorophenyl)-N'-(2,6-difluorobenzoyl)-urea (a) In a three-necked flask, 0.62 g of sodium azide in 30 ml of chlorobenzene were heated to 120° C. while stirring. At this temperature, first one third of a solution of 1.9 g of 2,3,4-trifluoro-5-chlorobenzoylfluoride in 10 ml of chlorobenzene was added dropwise. After a few minutes, when the evolution of nitrogen had started, the remainder of the solution was added dropwise within 10 minutes. During this time, the evolution of nitrogen became lively. When it stopped, the mixture was allowed to react for a half hour more. After cooling to 25° C., 0.5 g of kieselguhr were added, and the mixture was suction-filtered. The filtrate, which was a solution of 2,3,4-trifluoro-5-chlorophenylisocyanate in chlorobenzene, was used for the next reaction step.

(b) The filtrate from (a) was mixed with 1.42 g of 2,6-difluorobenzamide, which had previously been dried for 3 hours at 60° C. in vacuo, and the mixture was heated at about 100° C., while stirring, until a clear solution had formed. The solution was then stirred for 7 hours at 100° C. It was allowed to cool to 70° C. and was then evaporated to dryness in vacuo. The residue was stirred with 30 ml of acetone at 40° to 50° C., cooled to 10° C., suction-filtered and dried.

Yield: 2.1 g (64% of theory), m.p. 222°–224° C., of the title compound.

(c) The precursor, 2,3,4-trifluoro-5-chlorobenzoyl fluoride (b.p. 67 mbar: 97°–100° C.), was obtained in addition to 2,4-difluoro-3,5-dichlorobenzoyl fluoride (b.p. 67 mbar: 127°–129° C.) when 41.7 g of 2,3,4,5-tetrachlorobenzoyl chloride were heated at 200° C. with 43.5 g of potassium fluoride in 450 ml of sulfolane for 8 hours, and the reaction mixture was distilled in vacuo.

EXAMPLE 2

N-(2,4-Difluoro-3,5-dichlorophenyl)-N-(2,6-difluorobenzoyl)-urea (a) 2,4-Difluoro-3,5-dichlorobenzoyl fluoride Analogous to Example (1b), the title compound was obtained with a yield of more than 70% by reacting 2,3,4,5-tetrachlorobenzoyl chloride with potassium fluoride in sulfolane. The reaction temperature was 150° C., and the reaction time was 8 hours.

(b) Reaction of 2,4-difluoro-3,5-dichlorobenzoyl-fluoride with sodium azide 11.45 g of 2,4-difluoro-3,5-dichlorobenzoyl fluoride was added dropwise to a suspension of sodium azide (3.25 g) in toluene (40 ml) heated to about 100° C., and the course of the reaction was monitored by means of the nitrogen gas given off. After all the acid fluoride had been added the mixture was stirred for another hour at 110° C., during which sodium fluoride crystals were precipitated.

(c) Reaction of 2,4-difluoro-3,4-dichlorophenylisocyanate with 2,6-difluorobenzamide 7.9 g of 2,6-Difluorobenzamide were added to the suspension obtained in (b), and the reaction mixture allowed to stand for 10 hours at about 95° C. A white crystalline slurry precipitated during that time. After cooling, the precipitate was separated by suction filtration. 18.45 g of a mixture of sodium fluoride and benzoyl urea were isolated. The crude product thus obtained was extracted with boiling acetone and filtered. 16.2 g of N-(2,4-difluorobenzoyl)-urea were isolated from the filtrate (84.36% of theory).

EXAMPLE 3

N-(2,4-Difluoro-3,5-dichlorophenyl)-N'-(2,6-difluorobenzoyl)-urea

A solution of 23 g (0.100 mol) of 2,4-difluoro-3,5-dichlorobenzoyl fluoride in 100 ml of chlorobenzene was slowly added dropwise to a hot (125° C.) mixture of 7.0 g (0.105 mol) of sodium azide and 300 ml of chlorobenzene, while vigorously stirring. Nitrogen was given off. For safety reasons, the addition is regulated so that the quantity of benzoyl fluoride added dropwise corresponds to the rate of rearrangement of the Curtius degradation, which can be monitored by means of the nitrogen given off.

After all of the solution had been added, the mixture was allowed to react for 30 minutes more, then 3 g of kieselguhr were added, the mixture was allowed to cool to about 30° C., and the insoluble matter is suction-filtered off.

15.7 g (0.10 mol) of 2,6-difluorobenzamide were added to the filtrate and the mixture was heated at 100° C. for about 7 hours. The reaction mixture was worked up as described in Example 1.

Yield: 28.8 g (75.3% of theory), m.p. 221°–224° C., of the title compound.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing the compound of the formula

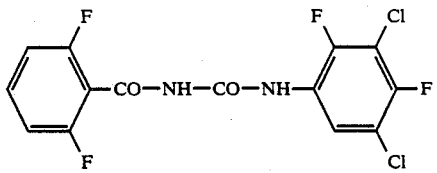

which comprises reacting a benzoyl derivative of the formula

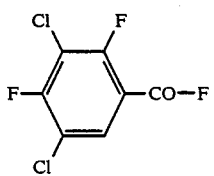

in an inert solvent said benzoyl derivative and inert solvent forming a reaction mixture, at elevated temperatures of between about 80° C. and the boiling point of the reaction mixture, with an alkali metal azide or an alkaline earth metal azide to form the azide intermediate of the formula

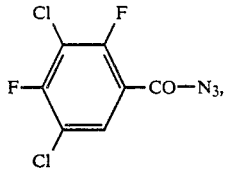

thermally degrading, at a temperature between about 80° C. and the boiling point of the reaction mixture, said azide intermediate in situ in the reaction mixture to form the isocyanate intermediate of the formula

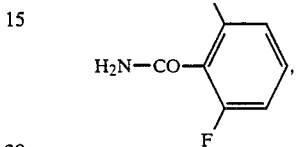

reacting said isocyanate intermediate in situ in the reaction mixture at elevated temperatures with the benzamide of the formula $$H_2N-CO-\underset{F}{\underset{|}{\overset{F}{\overset{|}{C_6H_3}}}},$$

and recovering the reaction product.

2. The method of claim 1, wherein said inert solvent is chlorobenzene.

* * * * *